United States Patent
Sakai

(10) Patent No.: US 8,187,185 B2
(45) Date of Patent: May 29, 2012

(54) ULTRASOUND DIAGNOSTIC APPARATUS

(75) Inventor: Ryoichi Sakai, Mitaka (JP)

(73) Assignee: Hitachi Aloka Medical, Ltd., Tokyo (JP)

( * ) Notice: Subject to any disclaimer, the term of this patent is extended or adjusted under 35 U.S.C. 154(b) by 951 days.

(21) Appl. No.: 11/835,832

(22) Filed: Aug. 8, 2007

(65) Prior Publication Data

US 2009/0043207 A1 Feb. 12, 2009

(51) Int. Cl.
*A61B 8/00* (2006.01)
(52) U.S. Cl. .................. 600/438; 600/437
(58) Field of Classification Search .......... 600/437, 600/438
See application file for complete search history.

(56) References Cited

U.S. PATENT DOCUMENTS

| 4,976,267 | A  | * | 12/1990 | Jeffcott et al. | 600/437 |
| 5,474,070 | A  |   | 12/1995 | Ophir et al.    |         |
| 6,221,019 | B1 | * | 4/2001  | Kantorovich     | 600/449 |
| 7,537,566 | B2 | * | 5/2009  | Mano et al.     | 600/442 |
| 2005/0133804 | A1 |   | 6/2005 | Hsu et al.      |         |
| 2005/0182325 | A1 | * | 8/2005 | Mano et al.     | 600/437 |
| 2006/0074311 | A1 | * | 4/2006 | Sakai et al.    | 600/437 |
| 2006/0241447 | A1 | * | 10/2006 | Harada et al.  | 600/443 |

FOREIGN PATENT DOCUMENTS

| EP | 1 639 946 A1 | 3/2006 |
| EP | 1 707 124 A2 | 10/2006 |
| JP | 2001309918 A | 11/2001 |
| JP | 2004298205 A | 10/2004 |
| JP | 2005165332 A | 6/2005 |
| WO | 2004/025541 A1 | 3/2004 |

OTHER PUBLICATIONS

European Search Report dated Dec. 3, 2007, Application No. 07014795.4-2305.

* cited by examiner

*Primary Examiner* — Tse Chen
*Assistant Examiner* — Peter Luong
(74) *Attorney, Agent, or Firm* — Westerman, Hattori, Daniels & Adrian, LLP

(57) ABSTRACT

The present invention provides an ultrasound diagnostic apparatus capable of appropriately evaluating dynamic characteristics of a bone. The ultrasound diagnostic apparatus obtains an interpolated line 52a representing a bone surface shape based on echo signals obtained from ultrasonic beams transmitted to a surface of the bone on which a load is applied. A user inputs an outer diameter φ of the bone which can be stored in a memory. The ULTRASOUND DIAGNOSTIC APPARATUS calculates a distortion ε which represents an expansion/contraction rate in an axial direction on the bone surface to which the load is applied, based on the interpolated line 52a and the bone outer diameter φ. The distortion ε is equal to a ratio defined by $x/(x+dx)=r/(r+dr)=r/(r+1/2\phi)$, wherein x represents a length of the bone surface in a measurement range (i.e., length of the interpolated line 52a) and x+dx represents a length of a neutral axis 52b of the bone.

8 Claims, 7 Drawing Sheets

ULTRASOUND DIAGNOSTIC APPARATUS

BACKGROUND OF THE INVENTION

1. Field of the Invention

The present invention relates to an ultrasound diagnostic apparatus, and more particularly to an ultrasound diagnostic apparatus which can be used for evaluation of dynamic characteristics of a diagnosed bone.

2. Description of the Related Art

Easy quantitative measurement of mechanical characteristics such as bone strength is desired for diagnosing bone metabolic diseases such as osteoporosis, judging fracture risk, and quantitatively diagnosing bone union after treatment of bone fracture.

The evaluation of bone formation and bone union depends largely on X-ray photography, but quantitatively diagnosing bone strength by means of X-ray photography is very difficult. The X-ray irradiation may also have adverse effects on a measurement target.

To evaluate dynamic characteristics of a bone, the ultrasound diagnostic apparatus discussed in Japanese Patent Laid-Open Publication No. 2004-298205 forms ultrasonic beams on the bone (i.e., measurement target), obtains echo signals corresponding to the individual ultrasonic beams to specify surface points corresponding to a bone surface for respective echo signals, and generates shape data of the bone surface based on the surface points obtained from the echo signals. Moreover, the apparatus calculates a distortion of the bone subjected to an external load based on the obtained shape data, and uses the obtained distortion value as a reference value in the measurement of bone strength, or determination of cured state of a fractured bone. The distortion obtained in this manner is a numerical value that can be used as an evaluation reference. Thus, the ultrasound diagnostic apparatus can realize a quantitative measurement of bone strength based on the obtained distortion.

However, the ultrasound diagnostic apparatus discussed in Japanese Patent Laid-Open Publication No. 2004-298205 calculates a distortion representing a position change rate in the radial direction of a diagnosed bone. More specifically, the apparatus obtains a distortion $\epsilon$ defined by a formula $\epsilon = \Delta d/L$ when L represents the length of a measurement range and $\Delta d$ represents a maximum displacement (i.e., maximum deflection) of a diagnosed bone in the radial direction when an external load is applied thereon. Namely, according to the Japanese Patent Laid-Open Publication No. 2004-298205, any factors other than a shape change on the bone surface (e.g., thickness of bone, cross-sectional shape, etc) are not taken into consideration.

Therefore, if two measurement targets mutually compared are different in the thickness of bone, their measurement results cannot be directly compared. As a result, evaluating the cured state of a fractured bone may fail if distortion data of a healthy bone having the same thickness is unavailable.

In view of the above circumstances, the present invention provides an ultrasound diagnostic apparatus capable of appropriately evaluating dynamic characteristics of a bone.

SUMMARY OF THE INVENTION

According to an aspect of the present invention, an ultrasound diagnostic apparatus can transmit an ultrasonic beam to a bone of a diagnosis object and diagnose dynamic characteristics of the bone. The ultrasound diagnostic apparatus includes a position data acquirement unit configured to acquire position data of a bone surface in a state where an external load is applied on the bone based on an echo signal obtained from an ultrasonic beam transmitted to the bone surface of a target body, a storage unit configured to store bone shape data including bone thickness information, and a calculation unit configured to calculate a distortion representing a change rate in an axial length of the bone based on the position data of the bone surface and the bone shape data.

It is preferable that the change rate in the axial length of the bone is equal to a ratio of the radius of an arc representing the bone surface to the radius of an arc representing a neutral axis of the bone in the state where the external load is applied on the bone. In this case, the bone shape data includes sectional shape information of the bone, and a method for calculating the arc radius representing the neutral axis is variable depending on the sectional shape information of the bone. Furthermore, a bone type of the diagnosis object is treated as the sectional shape information of the bone.

The ultrasound diagnostic apparatus according to the present invention calculates a distortion based on the bone shape data including bone thickness information. Thus, the obtained distortion reflects individual differences, such as thickness of bone, and accordingly can be appropriately used to evaluate dynamic characteristics of a diagnosed bone.

BRIEF DESCRIPTION OF THE DRAWINGS

Exemplary embodiments of the present invention will be described in detail based on the following figures, wherein.

DESCRIPTION OF PREFERRED EMBODIMENTS

Figure 1:
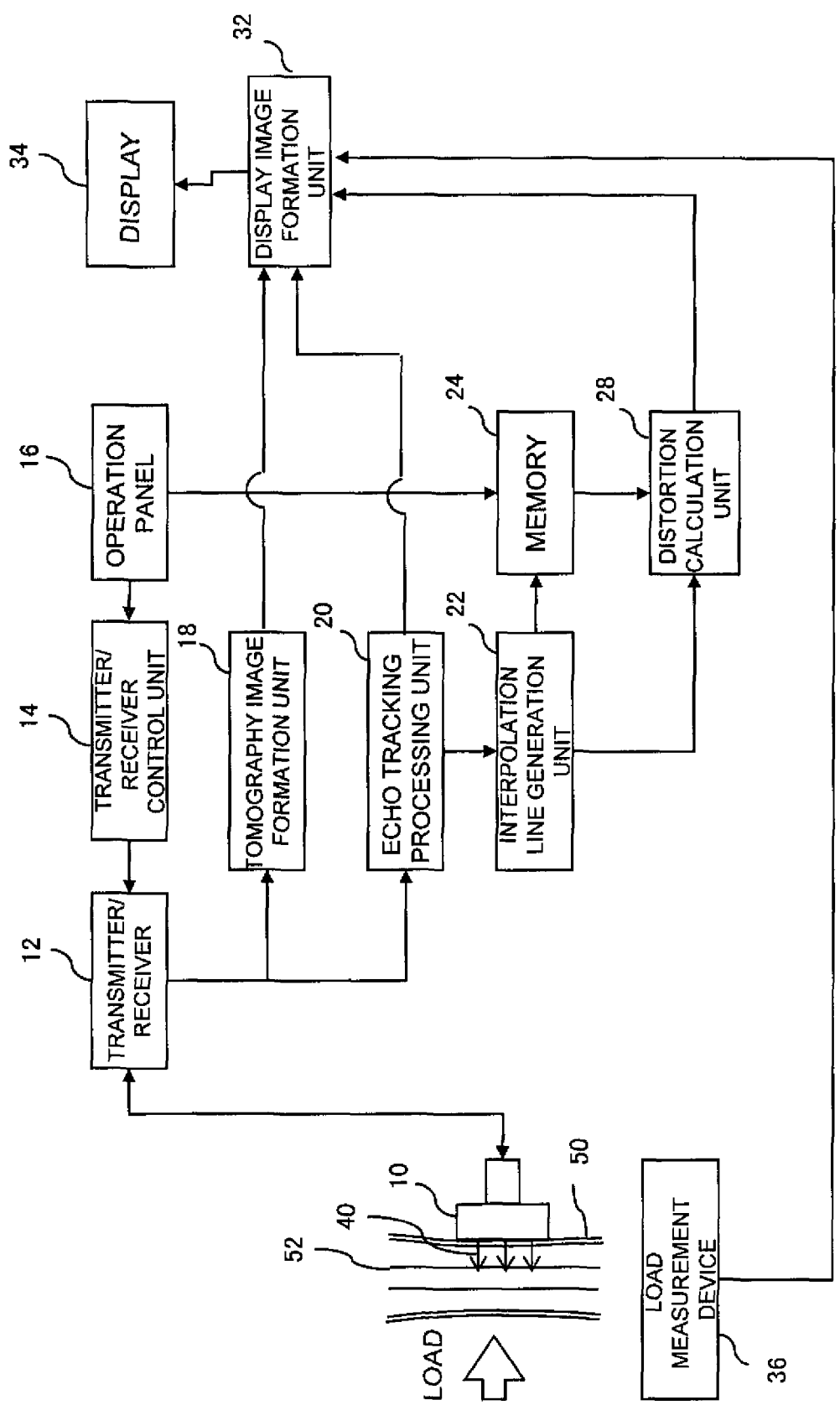
FIG. 1 is a block diagram illustrating an ultrasound diagnostic apparatus according to an embodiment of the present invention.

An embodiment of the present invention is described below in detail with reference to the drawings. FIG. 1 is a block diagram illustrating an ultrasound diagnostic apparatus according to an embodiment of the present invention, which is preferably used in the diagnosis of bone dynamic characteristics. In the present embodiment, an external load is applied to a bone (i.e., a diagnosis object) and a distortion of the bone is used as an index representing the bone dynamic characteristics. In other words, the ultrasound diagnostic apparatus is usable for measuring distortion data of a bone.

The ultrasound diagnostic apparatus according to the present embodiment includes an ultrasonic probe 10 which is brought into contact with a body surface 50 of a measurement target. If desirable, the probe 10 can be replaced with any other type of ultrasonic probe which may be located inside the body of the measurement target. The probe 10 has the capability of emitting ultrasonic beams 40 formed on a bone 52 in the body of the measurement target.

A transmitter/receiver 12 controls the probe 10 that performs electric scanning with ultrasonic beams 40 on a tomography surface. For example, if the probe 10 is a linear probe, a total of 120 ultrasonic beams 40 are successively emitted from the probe 10 for electric scanning. The transmitter/receiver 12 obtains an echo signal from each ultrasonic beam 40. A transmitter/receiver control unit 14 controls the transmitter/receiver 12 according to a user's instruction input via an operation panel 16.

The transmitter/receiver 12 outputs plural echo signals being thus obtained to a tomography image formation unit 18. The tomography image formation unit 18 forms a tomography image (B-mode image) of a target bone based on the plural echo signals. The transmitter/receiver 12 also outputs the obtained echo signals to an echo tracking processing unit 20. The echo tracking processing unit 20 performs echo tracking processing (i.e., extracting bone surface portions from the echo signals and perform tracking). For example, a technique discussed in Japanese Patent Laid-Open Publication No. 2001-309918 can be used for the echo tracking processing. The echo tracking processing uses a plurality of (e.g., three) tracking echo signals. The tracking echo signals can be selected from echo signals used for tomography image formation (e.g., 120 echo signals) Alternatively, three echo signals dedicated to the tracking can be used if available during interruption of the tomography image formation.

Figure 2:
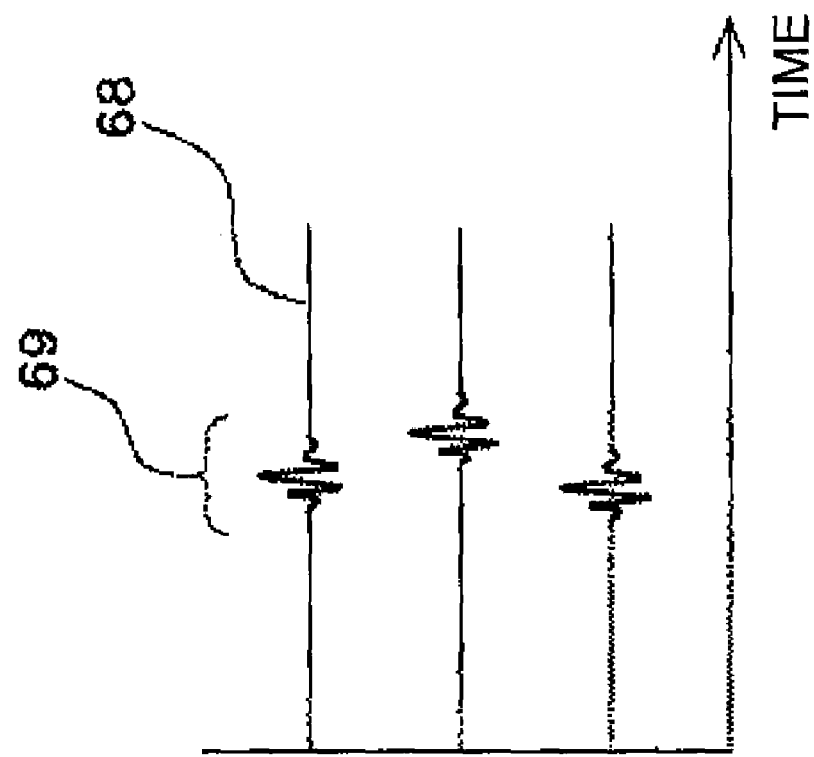
FIG. 2 illustrates exemplary tracking processing.
Figure 2:
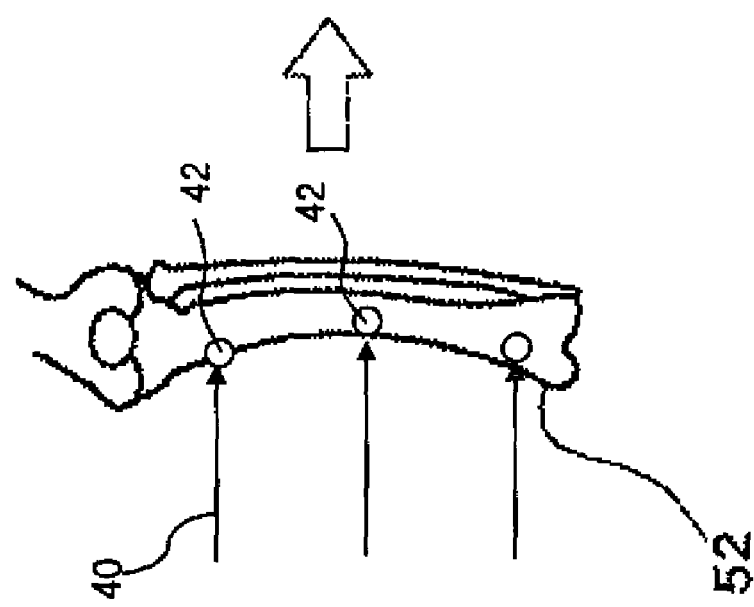

FIG. 2 illustrates exemplary tracking processing for obtaining three echo signals from a surface portion of the bone 52. An echo signal 68, corresponding to each ultrasonic beam 40 emitted toward the bone 52, has a large value in amplitude (i.e., an amplitude maximized portion 69) at a portion corresponding to the bone surface. The echo tracking processing unit 20 specifies the position of a bone surface based on the position of the amplitude maximized portion 69 (i.e., acquiring timing of a corresponding waveform).

Although the exemplary tracking illustrated in FIG. 2 uses three echo signals for echo tracking, any number of echo signals greater than one can be used for the measurement. In the echo tracking processing, a surface point tracked for each echo signal, i.e., for each ultrasonic beam 40, is referred to as a tracking point 42.

An interpolation line generation unit 22 (illustrated in FIG. 1) generates an interpolated line connecting these tracking points 42. Namely, the interpolation line generation unit 22 generates an interpolated curve connecting plural tracking points 42 based on the spline interpolation or the least squares method interpolation. The generated interpolated line (i.e., a curve) represents the shape of a target bone surface. An interpolated line, which can more accurately represent the target bone surface shape, can be obtained if the number of echo signals for the echo tracking processing is increased. The generated interpolated line can be temporarily stored in a memory 24 for use in the calculation of distortion $\epsilon$.

A distortion calculation unit 28 calculates distortion $\epsilon$ of a bone in a state where an external load is applied to the bone. More specifically, the distortion calculation unit 28 calculates the distortion $\epsilon$ based on the interpolated line and bone shape data input via the operation panel 16 from a user. The calculation method of the distortion $\epsilon$ will be described later.

Figure 3:
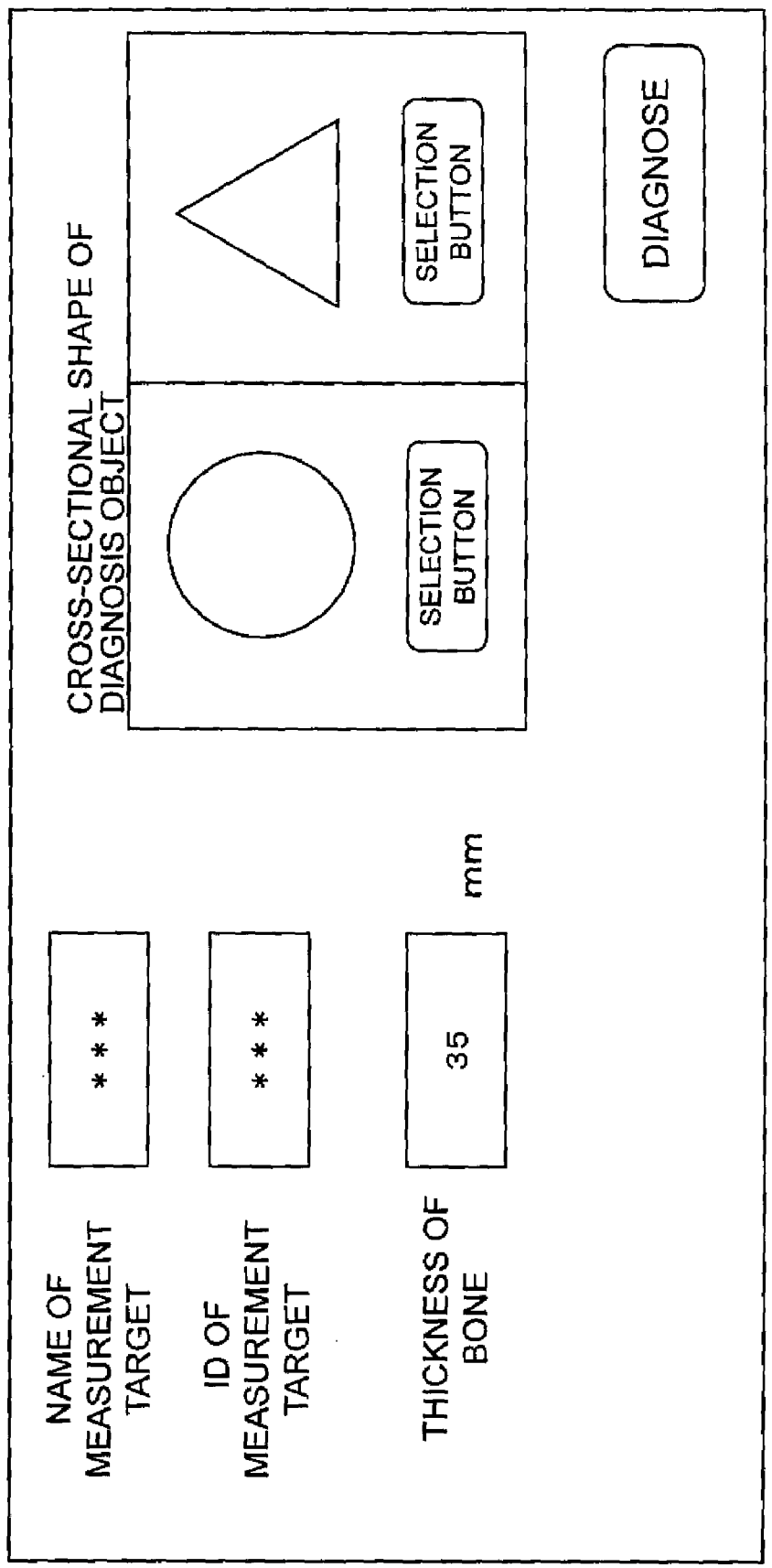
FIG. 3 illustrates an example of screen display for enabling a user to input bone shape data.

The bone shape data includes bone thickness information and sectional shape information of a diagnosis object. FIG. 3 illustrates an example of screen display for enabling a user to input bone shape data. A user, who wants to diagnose the dynamic characteristics of a bone, can input required data/information including name (i.e., name of measurement target), identification (i.e., ID of measurement target), thickness of bone (i.e., diagnosis object), and cross-sectional shape of bone (i.e., diagnosis object), according to the screen display illustrated in FIG. 3. The input bone shape data can be temporarily stored in the memory 24 for use in the calculation of distortion $\epsilon$.

Figure 4:
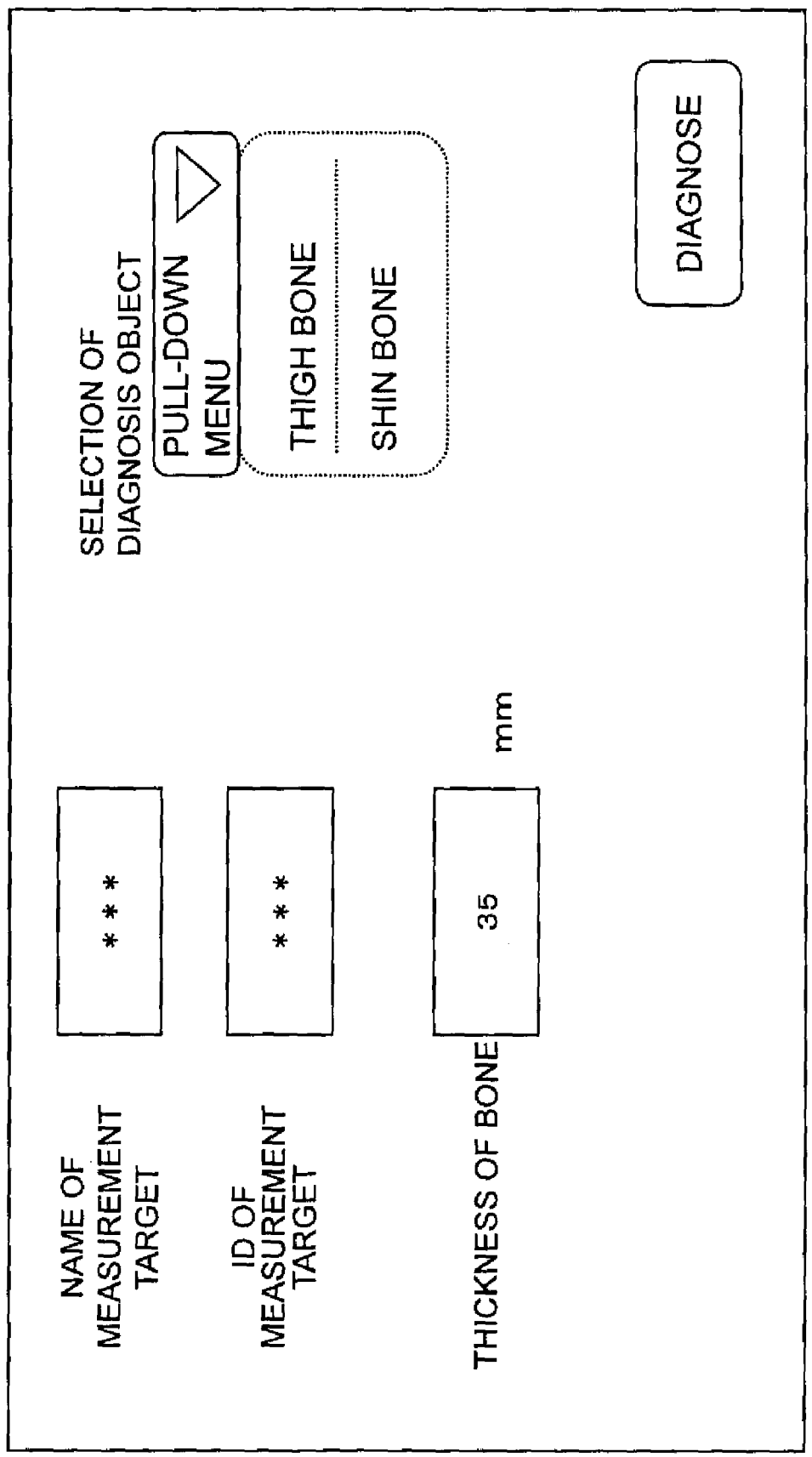
FIG. 4 illustrates another example of the screen display.

The thickness of a bone can be measured beforehand with an image diagnosing apparatus using an X-ray (e.g., X-ray tube or CT), or can be calculated based on a B-mode image obtained by the ultrasound diagnostic apparatus. The cross-sectional shape of a bone is dependent on the type of the bone and does not reflect individual differences. For example, the cross-sectional shape of a thighbone is substantially a circle. The cross-sectional shape of a shinbone is substantially an equilateral triangle. Accordingly, a user can select a corresponding bone type (i.e., the shape of the diagnosis object) as a cross-sectional shape of the bone. FIG. 4 illustrates another example of the screen display, according to which a user can select a graphic pattern representing the type of a bone. In this case, the ultrasound diagnostic apparatus determines a cross-sectional shape of the bone based on the selected graphic pattern.

A display image formation unit 32 forms an image, as a diagnosis result, to be displayed on a display 34. The display image formation unit 32 receives a tomography image from the tomography image formation unit 18, the distortion $\epsilon$ from the distortion calculation unit 28, and a load value applied to the bone which can be measured by a load measurement device 36. The display image formation unit 32 forms an image including a graph indicating a relationship between the distortion $\epsilon$ and the applied load. If desirable, the display image formation unit 32 further combines the obtained graph image with the B-mode image. Then, the display image formation unit 32 outputs a resultant image as a display image to the display 34.

Figure 5A:
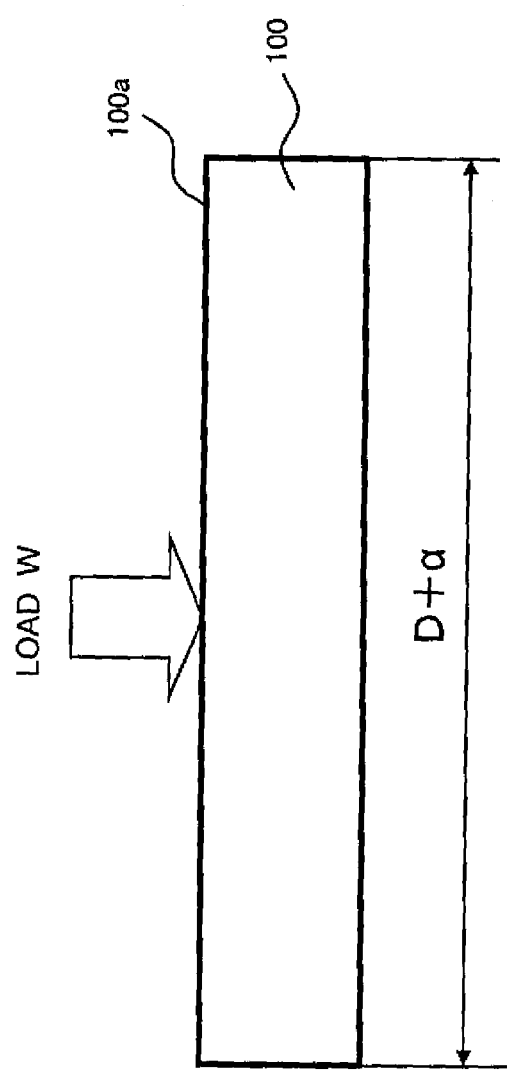
FIG. 5A illustrates the shape of a bar in a state where no load is applied.
Figure 5B:
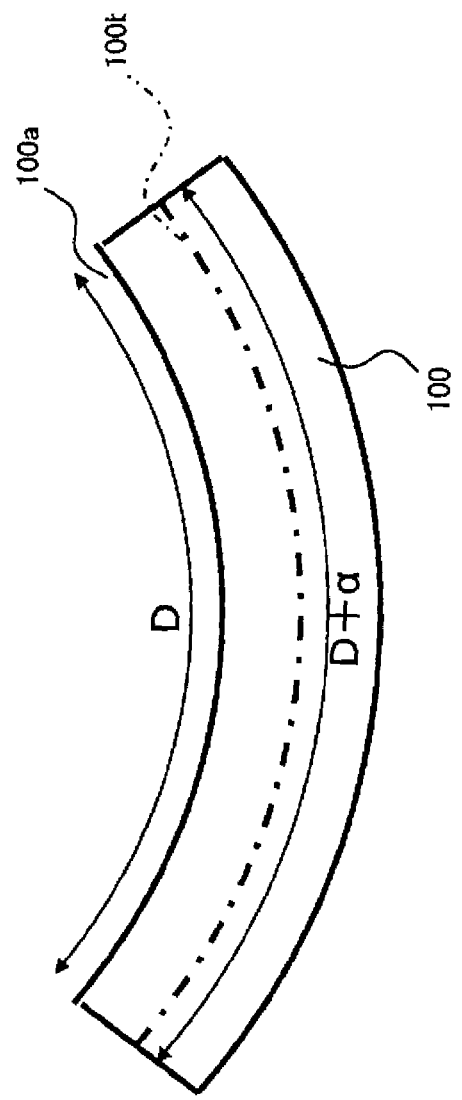
FIG. 5B illustrates the shape of a bar in a state where a load is applied.

The distortion $\epsilon$ (i.e., index of bone diagnosis) is described below in more detail. The distortion $\epsilon$ is a value representing expansion/contraction characteristics of a member deformed when an external load is applied on this member, and can be used as an index evaluating strength. In the present embodiment, the distortion $\epsilon$ represents an expansion/contraction ratio in the axial direction. For example, as illustrated in FIGS. 5A and 5B, a bar 100 having a circular cross section deforms (deflects) into an arc shape when a load W is applied on an upper surface 100a of the bar 100. The upper surface 100a of the bar 100 contracts and causes a change in the length from D+$\alpha$ to D. In this case, the distortion $\epsilon$ of the upper surface 100a of the bar 100 is equal to a ratio of contraction $\alpha$ to original length D+$\alpha$, i.e., $\epsilon=\alpha/(D+\alpha)$.

In general, when a load is applied on an upper surface of a bar member, the upper surface of the bar member contracts while a lower surface expands. On the other hand, an intermediate portion of the bar member does not cause any change in the length. The portion causing no change in the length is referred to as neutral axis (indicated by 100b in FIG. 5B). The position of the neutral axis 100b varies depending on a cross-sectional shape of the member. If the cross-sectional shape is a circle, the neutral axis agrees with a line passing the center of this circle.

No expansion/contraction of the member is caused on the neutral axis 100b. The length of the neutral axis 100b is equal to the length of the upper surface 100a of the bar 100 in a no-load state. Accordingly, the distortion $\epsilon$ ($\epsilon=\alpha/D$) can be obtained based on the length of the neutral axis 100b and a length of the upper surface 100a of the bar 100 in a state where a load is applied to the bar 100. Thus, the present embodiment calculates the distortion $\epsilon$ of a bone in a loaded state according to this principle.

Figure 6:
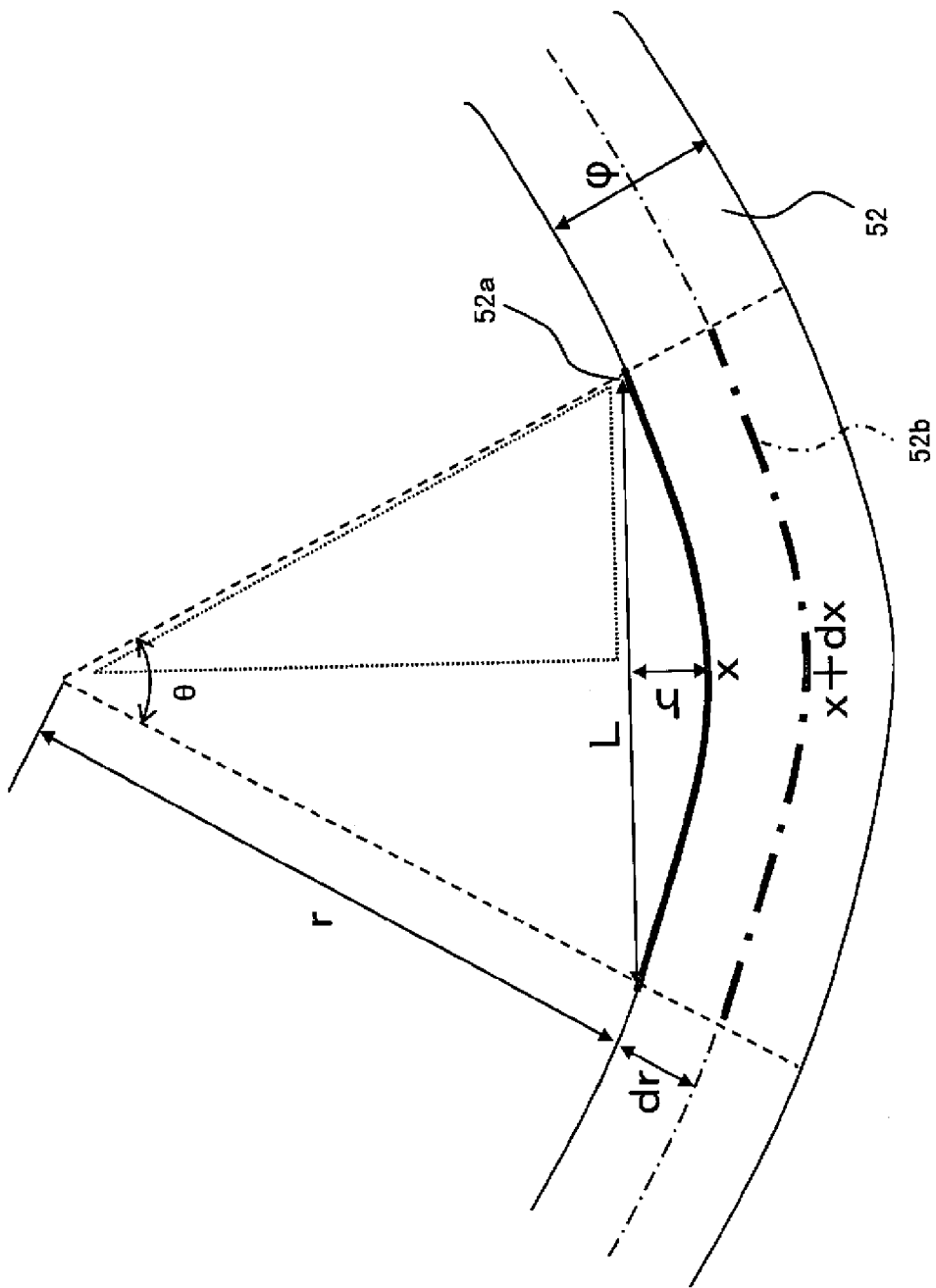
FIG. 6 illustrates parameters used in the calculation of a distortion generated in a bone.

An exemplary method for calculating the distortion ε of a thighbone having a substantially circular cross section is described below. FIG. 6 illustrates a deformed thighbone in a state where a load is applied thereto. The calculation of distortion ε includes transmitting ultrasonic beams on a surface of this bone, calculating the position of each tracking point on the bone surface based on each obtained echo signal, and interpolating the positions of the obtained tracking points to form an interpolated line 52a representing a bone surface shape (i.e., a bold line in FIG. 6).

In this example, the length L of the measurement range of the ultrasound diagnostic apparatus and a deflection h of the bone are sufficiently short compared to the entire length of the bone. Accordingly, a deflection shape of the bone in a measurement range can be presumed as an arc having a constant radius of curvature.

If x represents the length of a bone surface in the measurement range (i.e., the length of interpolated line 52a) and x+dx represents the length of the bone along the neutral axis (indicated by an alternate long and short dash line in FIG. 6), the distortion ε can be expressed using the following formula 1.

$$\epsilon = dx/(x+dx) \quad \text{formula 1}$$

As a deflected bone can be presumed to have an arc shape, two items dx and x+dx in formula 1 can be converted into a formula for an arc. Namely, if "r" represents the radius of an arc representing a bone surface (i.e., interpolated line: bold line) and "r+dr" represents the radius of an arc representing a bone neutral axis 52b (i.e., bold alternate long and short dash line), relationships dx=r·K and x+dx=(r+dr)·K are obtained with a definition K=2π·θ/360°. If these relationships are used to rewrite the formula 1, the following formula 2 can be obtained.

$$\epsilon = r/(r+dr) \quad \text{formula 2}$$

Furthermore, if the cross-sectional shape of a bone is substantially a circle, the neutral axis 52b agrees with the central point of a circle. Accordingly, if φ represents an outer diameter of the bone, the following formula 3 can be obtained.

$$dr = \phi/2 \quad \text{formula 3}$$

Furthermore, the following formula 4 can be derived from a right triangle indicated by a dotted line in FIG. 6 according to the Pythagorean theorem.

$$r^2 = \{(L/2)^2 + (r-h)^2\}$$

$$r = (L^2 + 4h^2)/8h \quad \text{formula 4}$$

Then, the following formula 5 can be obtained from the above-described formulas 2, 3, and 4.

$$\varepsilon = r/r + dr \quad \text{formula 5}$$
$$= 4h\varphi/(L^2 + 4h^2 + 4h\varphi)$$

In the formula 5, a right side is composed of known values. Namely, the deflection h and the measurement range length L can be obtained from the interpolated line. The bone outer diameter φ can be designated beforehand by a user. Thus, the distortion ε can be calculated based on known values according to the formula 5.

According to the above-described conventional technique, an index evaluating the bone dynamic characteristics is a ratio (h/L) of the deflection h to the measurement range length L. The ratio h/L does not include any factor relating to differences of individual bones, such as thickness of bone. Therefore, the ratio h/L cannot be directly used in the comparison between a measurement result of a diagnosis object and the measurement result of another object which has a different bone thickness. As a result, for example, if the data of a healthy bone having the same thickness is unavailable, the conventional apparatus cannot accurately diagnose the cured state of a fractured bone or cannot detect bone diseases (e.g., faulty union or osteomalacia).

On the other hand, the distortion ε obtained by the present embodiment is a diagnosis index reflecting the bone thickness, i.e., outer diameter φ, as is apparent from the formula 5. Therefore, the distortion ε (i.e., measurement result) of a diagnosis object can be accurately compared with the measurement result of other object which has a different bone thickness. As a result, the present embodiment can facilitate diagnosing the cured state of a fractured bone or bone diseases.

Figure 7B:
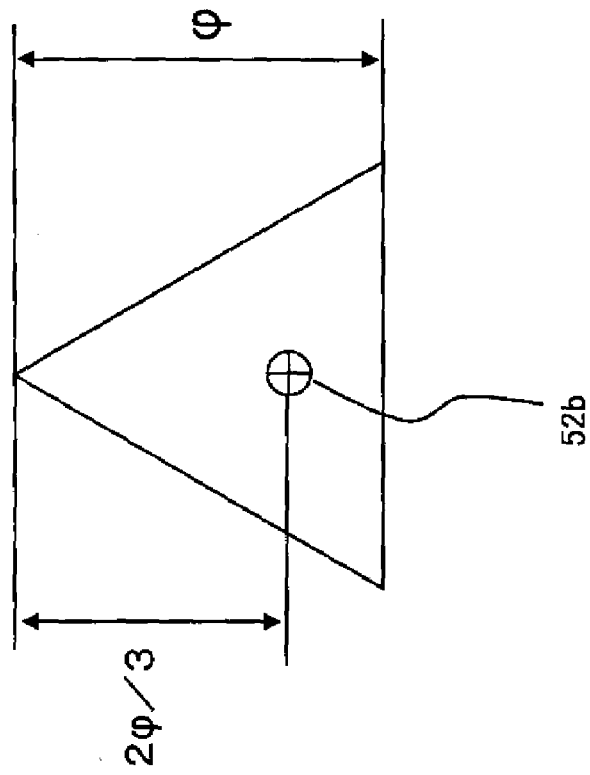
FIG. 7B illustrates the position of a neutral axis of a bar member having a triangular cross section.
Figure 7A:
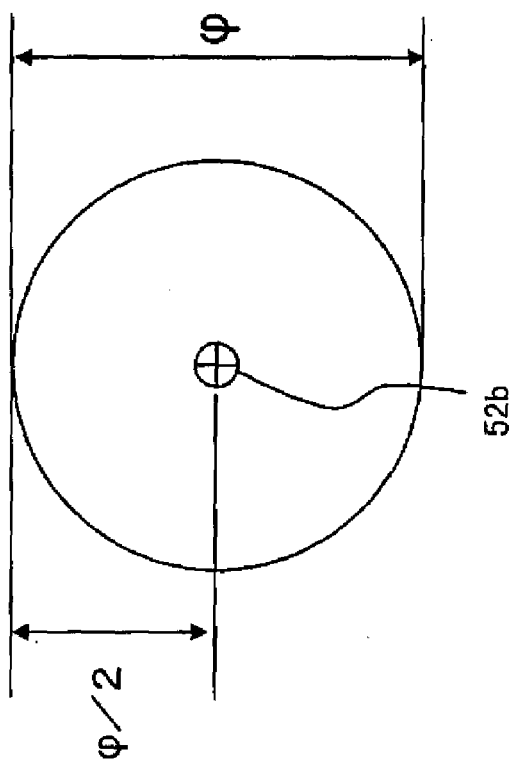
FIG. 7A illustrates the position of a neutral axis of a bar member having a circular cross section.

Although the above embodiment has been described with reference to a thighbone having a circular cross section, the present embodiment can be applied to any other bones, such as a shinbone having a triangular cross section. It is however desirable to change the value of dr according to a cross-sectional shape of each bone. For example, if a bone has a circular cross section as illustrated in FIG. 7A, the neutral axis 52b passes the center of the circle. If the cross section of a bone is substantially a right triangle as illustrated in FIG. 7B, the neutral axis 52b passes a 2/3 point of a perpendicular extending from a vertex of the triangle to which a load is applied. If a bone has such a triangular cross-sectional shape, dr is replaced with 2/3φ (i.e., dr=2/3φ), and the distortion ε is equal to $16h\phi/(3L^2+12h^2+16h\phi)$. In this manner, reliability of a calculated distortion value can be improved by adequately changing the calculation formula of the distortion ε according to a cross-sectional shape of each bone.

Next, an exemplary diagnosis using the distortion ε is described below. An exemplary diagnosis using the distortion ε is, for example, a diagnosis for detecting the cured state of a fractured bone. The diagnosis of a fractured bone (in the degree of bone union) includes measuring a distortion of a fractured bone periodically (e.g., once every two weeks), and comparing the measured distortion with a reference distortion (e.g., a distortion of a healthy bone having not been fractured). The diagnosis further includes determining that a diagnosed bone is sufficiently cured if the distortion of the fractured bone (i.e., diagnosis object) is substantially the same as the reference distortion. The distortion obtained in the present embodiment is a value reflecting the thickness of a bone. Therefore, the present embodiment can perform a proper diagnosis of a fractured bone even if the fractured bone (i.e., diagnosis object) has a thickness different from that of a healthy bone (serving as a reference distortion). As a result, the present embodiment does not require many reference values to be prepared for the comparison with various distortion values of fractured bones which are different in the thickness. Thus, the present embodiment enables a user to easily diagnose the cured state of a fractured bone.

Furthermore, the present embodiment enables a user to check a curing speed of each measurement target based on temporal changes of distortion in comparison with the data of another measurement target. The comparison of curing speeds between plural measurement targets may lead to early detection of various diseases which may delay the union of a fractured bone.

As described above, the present embodiment calculates the distortion ε considering individual differences, such as differences in thickness, between individual bones. The distortion ε calculated by the present embodiment can be used to compare two measurement targets which are different in the thickness of bone. Thus, the present embodiment can properly evaluate the bone dynamic characteristics. Furthermore, the present embodiment can improve the reliability of distortion $\epsilon$ (i.e., evaluation index) by taking a cross-sectional shape of the bone into consideration.

Although the preferred embodiments of the present invention have been described using specific terms, such description is for illustrative purposes only, and it is to be understood that modifications and variations may be made without departing from the spirit or scope of the appended claims.

What is claimed is:

1. An ultrasound diagnostic apparatus capable of transmitting an ultrasonic beam to a bone of a diagnosis object and diagnosing dynamic characteristics of the bone, comprising:
   a position data acquirement unit configured to acquire position data of a bone surface in a state where an external load is applied to the bone, based on an echo signal obtained from the ultrasonic beam transmitted to the bone surface of the diagnosis object;
   a storage unit configured to store predetermined bone shape data including bone thickness information of the diagnosis object; and
   a calculation unit configured to determine a change rate in an axial length along a major length of the bone calculated from at least the bone thickness information and the position data of the bone.

2. The ultrasound diagnostic apparatus according to claim 1, wherein the change rate in the axial length along a major length of the bone is further calculated from a ratio of a radius of an arc representing the bone surface to the radius of an arc representing a neutral axis of the bone, in the state where the external load is applied to the bone.

3. The ultrasound diagnostic apparatus according to claim 2, wherein the bone shape data includes the radius of the arc representing the neutral axis of the bone that corresponds to the cross-sectional shape information of the bone.

4. The ultrasound diagnostic apparatus according to claim 3, wherein a bone type of the diagnosis object is included in the cross-sectional shape information of the bone.

5. An ultrasound diagnostic method for diagnosing dynamic characteristics of a bone of a diagnosis object to which an ultrasonic beam is transmitted, said method comprising the steps of:
   acquiring position data of a bone surface of the bone of the diagnosis object in a state where an external load is applied to the bone, based on an echo signal obtained from the ultrasonic beam transmitted to the bone surface;
   storing predetermined bone shape data including bone thickness information of the diagnosis object; and
   determining a change rate in an axial length along a major length of the bone calculated from at least the bone thickness information and the position data of the bone surface.

6. The ultrasound diagnostic method according to claim 5, wherein the change rate in the axial length along a major length of the bone is further calculated from a ratio of a radius of an arc representing the bone surface to the radius of an arc representing a neutral axis of the bone, in the state where the external load is applied to the bone.

7. The ultrasound diagnostic method according to claim 6, wherein the bone shape data includes the radius of the arc representing the neutral axis of the bone corresponds to the cross-sectional shape information of the bone.

8. The ultrasound diagnostic method according to claim 7, wherein a bone type of the diagnosis object is included in the cross-sectional shape information of the bone.

* * * * *